United States Patent [19]
Graf

[11] Patent Number: 5,961,516
[45] Date of Patent: Oct. 5, 1999

[54] DEVICE FOR MECHANICALLY CONNECTING AND ASSISTING VERTEBRAE WITH RESPECT TO ONE ANOTHER

[76] Inventor: Henry Graf, 8, rue Duquesne, Lyons 69006, France

[21] Appl. No.: 08/900,866

[22] Filed: Jul. 25, 1997

[30] Foreign Application Priority Data

Aug. 1, 1996 [FR] France .................................. 96 09913

[51] Int. Cl.⁶ .................................................. A61B 17/56
[52] U.S. Cl. ............................... 606/61; 606/60; 606/62; 606/72; 623/17; 623/19
[58] Field of Search ..................... 606/60–75; 623/17–23

[56] References Cited

U.S. PATENT DOCUMENTS

| | | | |
|---|---|---|---|
| 5,375,823 | 12/1994 | Navas | 606/61 |
| 5,480,401 | 1/1996 | Navas | 606/61 |
| 5,540,688 | 7/1996 | Navas | 606/61 |
| 5,584,834 | 12/1996 | Errico et al. | 606/61 |
| 5,591,166 | 1/1997 | Bernhardt et al. | 606/61 |
| 5,628,740 | 5/1997 | Mullane | 606/61 |
| 5,709,685 | 1/1998 | Dombrowski et al. | 606/61 |

FOREIGN PATENT DOCUMENTS

| | | |
|---|---|---|
| 576379 | 12/1993 | European Pat. Off. . |
| 611554 | 8/1994 | European Pat. Off. . |
| 667127 | 8/1995 | European Pat. Off. . |
| 2697428 | 4/1994 | France . |

Primary Examiner—Michael Buiz
Assistant Examiner—Lien Ngo
Attorney, Agent, or Firm—Dowell & Dowell, P.C.

[57] ABSTRACT

A device for mechanically connecting and assisting vertebrae with respect to one another which includes at least one securing device cooperating with a ball joint adapted to be connect to a vertebra and a compressible body maintained along an axis of the securing device. The securing device includes two end bodies which retain a ball joint and the compressible element therebetween. At least one of the two end bodies is formed as a cup which is adapted to cover a portion of the ball joint and the end bodies are connected together by a connecting element disposed around the compressible member and over the cup of at least one of the two end bodies such that the connecting element is adapted to move over an outer surface of the cup.

26 Claims, 8 Drawing Sheets

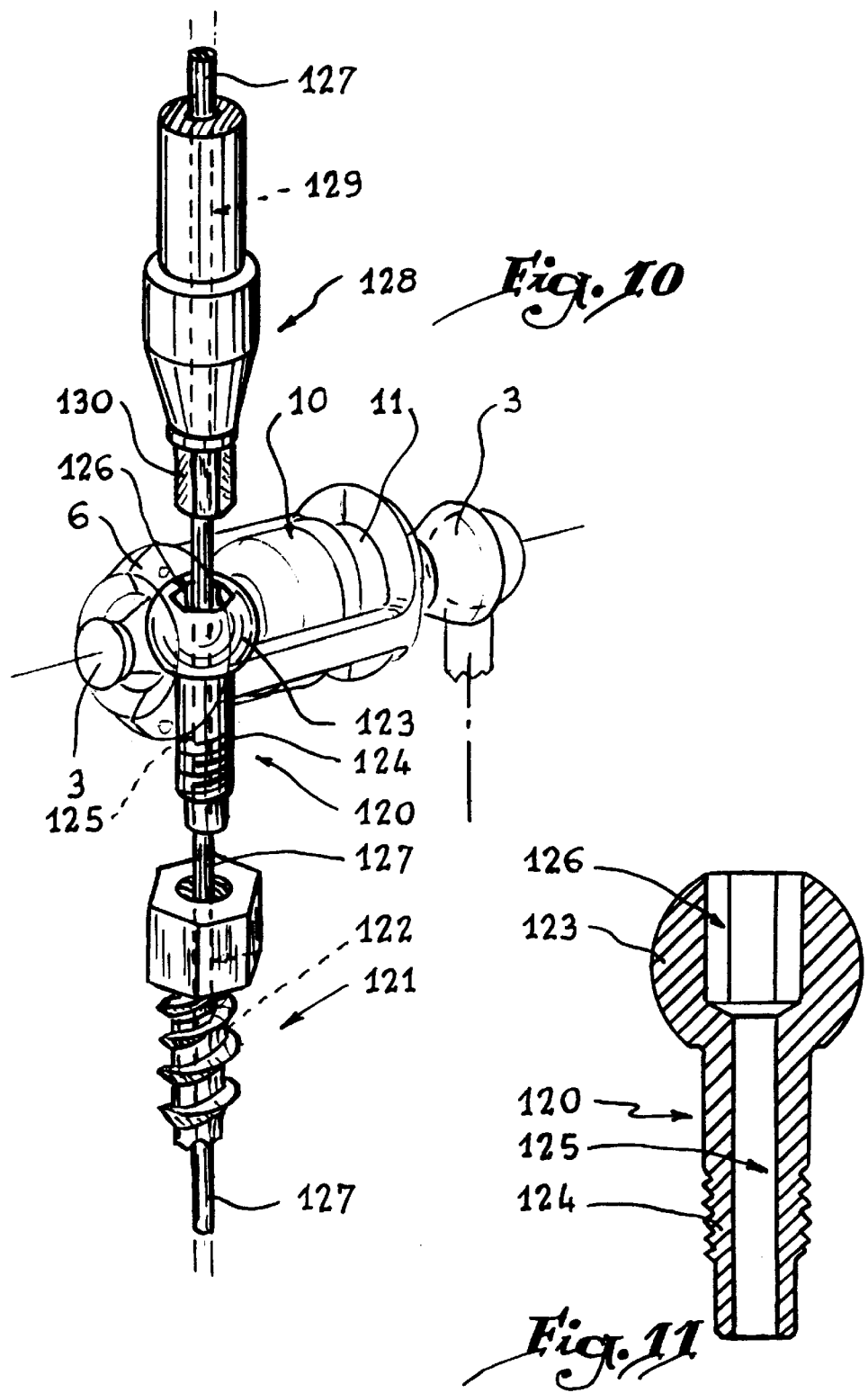

DEVICE FOR MECHANICALLY CONNECTING AND ASSISTING VERTEBRAE WITH RESPECT TO ONE ANOTHER

BACKGROUND OF THE INVENTION

1. Field of the Invention

The present invention relates to a device for mechanically connecting and assisting vertebrae with respect to one another, comprising at least one securing device presenting a ball joint extending from a vertebra and a compressible body maintained along the longitudinal axis of said securing device, said ball joint and said compressible element being housed between two end bodies of said securing device.

2. Brief Description of the Related Art

This type of device for mechanically connecting and assisting vertebrae with respect to one another acts outside the vertebral discs in order to compensate for defects of the spine, this making it possible to control and/or modify the movements of flexion and of traction between two vertebrae.

EP-A-0 611 554 discloses an intervertebral shock-absorber constituted by a cylindrical chamber receiving a ball joint extending from a vertebra, a piston capable of sliding in this cylindrical chamber as well as a compressible body. This cylindrical chamber is closed, at its end opposite the compressible body, by a screwed discoidal part. The volume of the elastic body, at rest, is less than that of the volume determined by the position of the piston with respect to the bottom of the cylindrical chamber.

This device allows a good intervertebral stabilization thanks to the presence of the compressible body which progressively resists the advance of the piston in exponential manner The connection between two devices of this type is effected by an assembly ring cooperating with tenons made on the corresponding ends of the cylindrical chambers.

In order to allow a relative movement in rotation between two adjacent securing devices, in the three dimensions in space, it is necessary that this assembly ring be made of a material allowing torsions in these three directions. This assembly member must therefore present a sufficient rigidity to connect two adjacent securing devices, as well as a considerable suppleness enabling it to twist in three directions. This compromise renders the design of such a ring very delicate, and its cost high.

In order to overcome these various drawbacks, the present invention aims at producing a device for mechanically connecting and assisting vertebrae, in which the securing devices may move mutually in rotation in the three directions in space, and which has a simple and reliable structure.

SUMMARY OF THE INVENTION

To that end, the invention relates to a device of the type mentioned above, characterized in that at least one of the end bodies is formed by a cup adapted to cover the ball joint, and in that the end bodies are connected together by a connecting element disposed around the compressible body and over at least one of the cups, the connecting element being adapted to move over the outer face of the cup.

The term cup is understood to mean an element whose inner face is substantially semi-spherical in order to cooperate with the ball joint, and whose outer face is likewise substantially semi-spherical in order to cooperate with the connecting element.

The device according to the invention makes it possible to realize the objects previously set forth. In fact, since the connecting element may move over the outer face of the cup, the two end bodies of each securing device are maintained in an axial direction but may move mutually in rotation in the three directions of space. Consequently, it is not necessary to employ an additional member allowing movement between the adjacent ends of two adjacent securing devices. These adjacent ends may for example be left secured. Being given that an additional member is no longer necessary, each securing device has greater longitudinal dimensions, which renders design thereof easier, increases solidity and improves efficiency thereof. In particular, the compressible body may be of larger dimensions than in the prior art According to a first variant of the invention, the connecting element of each securing device comprises a base from which extend three branches having, at their free ends, a surface for contact with the cup, a ring joining the branches together, while the base is provided with a housing cooperating with a finger of the compression chamber to constitute a bayonet-type locking device.

According to another variant of the invention, the connecting element of each securing device comprises a muff of which one of the ends includes a slot cooperating with a finger secured to the compression chamber to constitute a bayonet-type locking device, while, opposite the slot, the muff includes an oblong opening for the passage of the ball joint of the corresponding screw.

These embodiments employing a bayonet-type locking make it possible to maintain the compression chamber along its longitudinal axis, as well as a rotation of the connecting element with respect to this chamber, about this longitudinal axis.

Where a bayonet-type locking device is not used, the connecting element of each securing device may be constituted by two elements connected to each other around the compression chamber of the cup, via retaining pins.

This embodiment is considerably simple to manufacture and ensures an easily removable connection.

Where one of the end bodies is formed by a cap, the corresponding contact surfaces of the cap and of the connecting element are preferably substantially semi-spherical, which ensures self-adjustment of the compression chamber along its longitudinal axis.

According to another embodiment of the invention, the two end bodies are cups and the connecting element comprises two open elastic rings connected to each other by cross bars, each ring being disposed on the outer face of a corresponding cup. This embodiment is very simple, insofar as the elastic rings may both be maintained on the outer face of the cups, and be removed therefrom, by simple clipping.

According to an advantageous characteristic of the invention, the adjacent ends of two adjacent securing devices are made all in one piece, which appreciably simplifies manufacture. In this case, each end of a securing device is capable of moving in rotation in the three directions in space, with respect to the distal end of the adjacent securing device, which ensures a perfect possibility of relative movement between these two adjacent securing devices.

BRIEF DESCRIPTION OF THE DRAWINGS

The invention will be more readily understood on reading the following description with reference to the accompanying drawings, in which:

FIG. 10 is a partial perspective view illustrating a variant embodiment and assembly of the securing device, and FIG. 11 is an axial section of the ball joint shown in FIG. 10.

DESCRIPTION OF PREFERRED EMBODIMENTS

Figure 1:
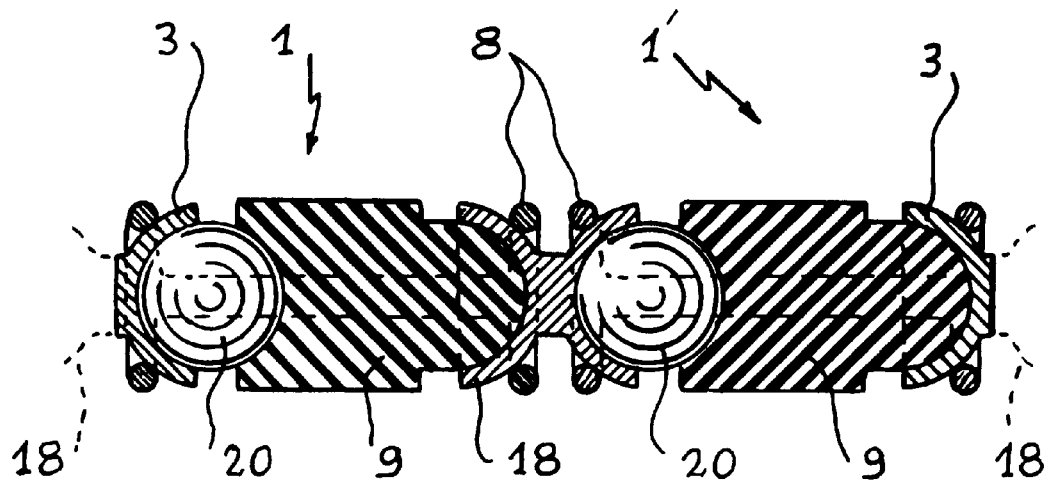
FIG. 1 is a view showing two securing devices constituting the device for connecting and assisting vertebrae with respect to one another.

Referring now to the drawings, and firstly to FIG. 1, a device according to the invention for mechanically connecting and assisting vertebrae with respect to one another is shown. It is constituted by two securing devices generally designated by references 1 and 1'.

Each securing device comprises a ball joint 20 extends from an intervertebral screw (not shown) which is previously implanted in a vertebra. A cup 3, forming a first end body, covers a first side of the ball joint 20. A compressible body 9 is disposed on the side of the ball joint opposite the cup 3. This compressible body is an elastic body capable of modifying its width upon the action of an effort of compression. It cooperates with the ball joint 20 via a corresponding semi-spherical cavity. The compressible body is in addition covered, at its end opposite the ball joint, by a cup 18 forming a second end body of the securing device 1.

Figure 2:
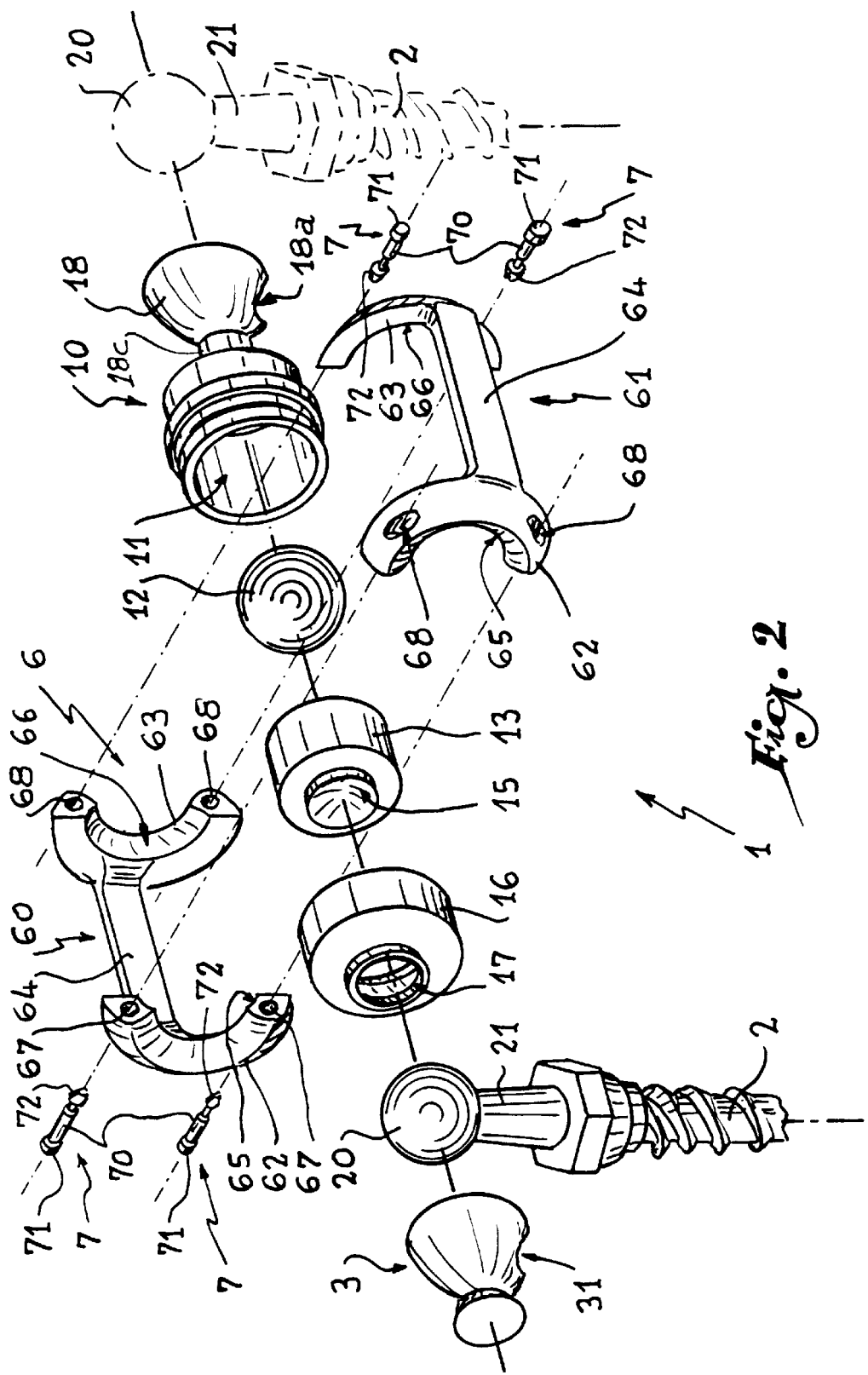
FIG. 2 is an exploded view in perspective showing a variant of a securing device.
Figure 3:
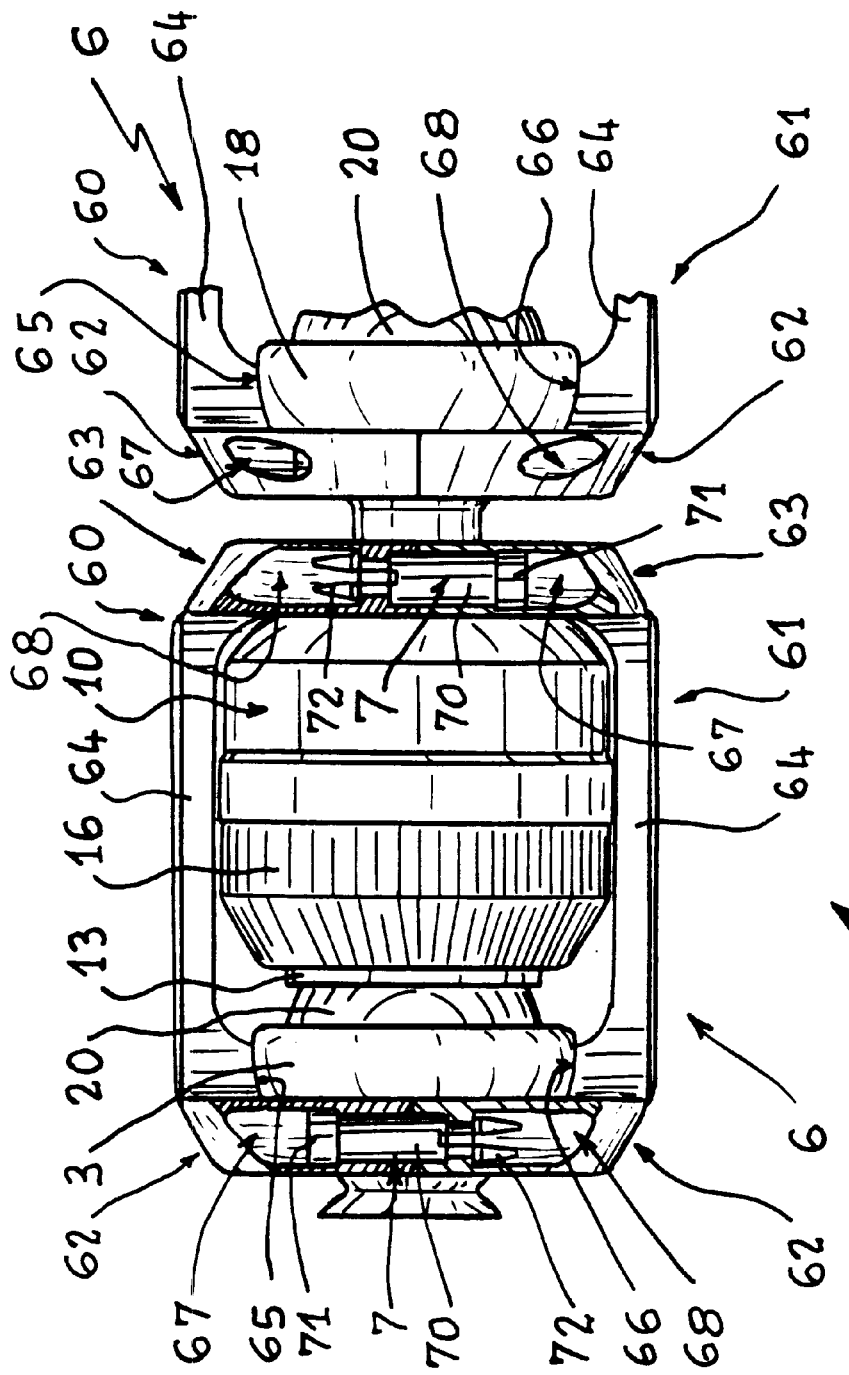
FIG. 3 is a view representing the securing device of FIG. 2 in assembled position.

The end cups 3, 18 are connected together via a connecting element 6 in accordance with the one illustrated in FIGS. 2 and 3. This connecting element 6 is capable of moving over the outer faces of the cups 3, 18 so that the latter, while being connected in a substantially axial direction A—A, are capable of moving mutually in rotations in the three directions in space.

Cup 18 extends, opposite ball joint 20, in a cup 3', similar to cup 3, which constitutes a first end body of the second securing device 1', this latter being similar to the device 1 described hereinabove.

In accordance with the invention, the two securing devices 1, 1' are capable of moving mutually in rotation in the three directions in space.

Figure 1A:
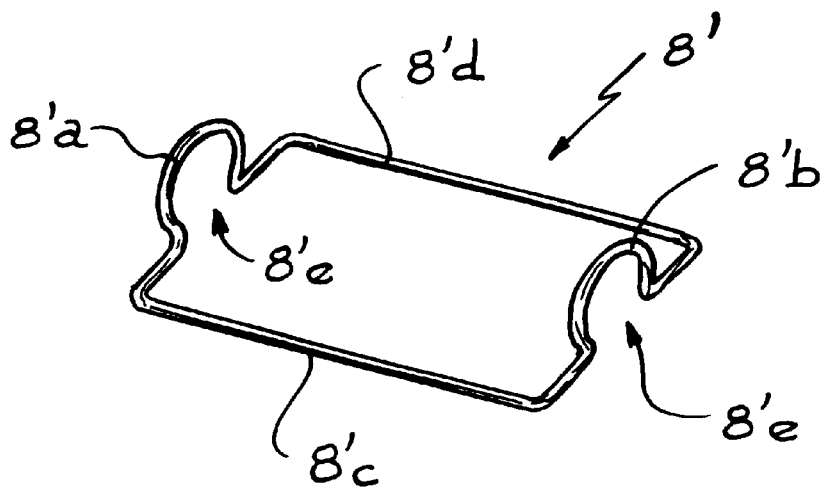
FIG. 1a is a view illustrating a variant of the connecting element of each securing device according to the invention.

The connecting element 6 of each securing device 2 may be replaced by the element 8' shown in FIG. 1a. The latter comprises two opposite open rings 8'a and 8'b connected together by parallel cross bars 8'c and 8'd. The rings 8'a and 8'b each have an opening 8'e of dimensions smaller than those of the narrowed portion 33, 18c of cups 3 and 18, to allow fixation by elastic deformation of the connecting element 8'.

FIGS. 2 and 3 show a variant embodiment in which each securing device 1 comprises a cup 3 forming a first end body, which covers a ball joint 20 of an intervertebral screw or hook 2 previously implanted in a vertebra. A cap 11 forming a second end body cooperates with a sleeve 16 to form a compression chamber 10. The latter receives an elastic or compressible body 12 whose volume is less than that of the cap 11 of the chamber 10. The elastic body 12 takes a spherical or like shape, deformable upon movements in flexion/traction between two vertebrae of a spine. The combination of at least two securing devices 1 allows a better control of the efforts applied longitudinally along the axis of the compressible body. In fact, the securing devices I according to the invention allow the transformation into compression of any effort applied longitudinally to the axis of the compressible body, whether the effort be a traction and/or a compression.

Figure 4:
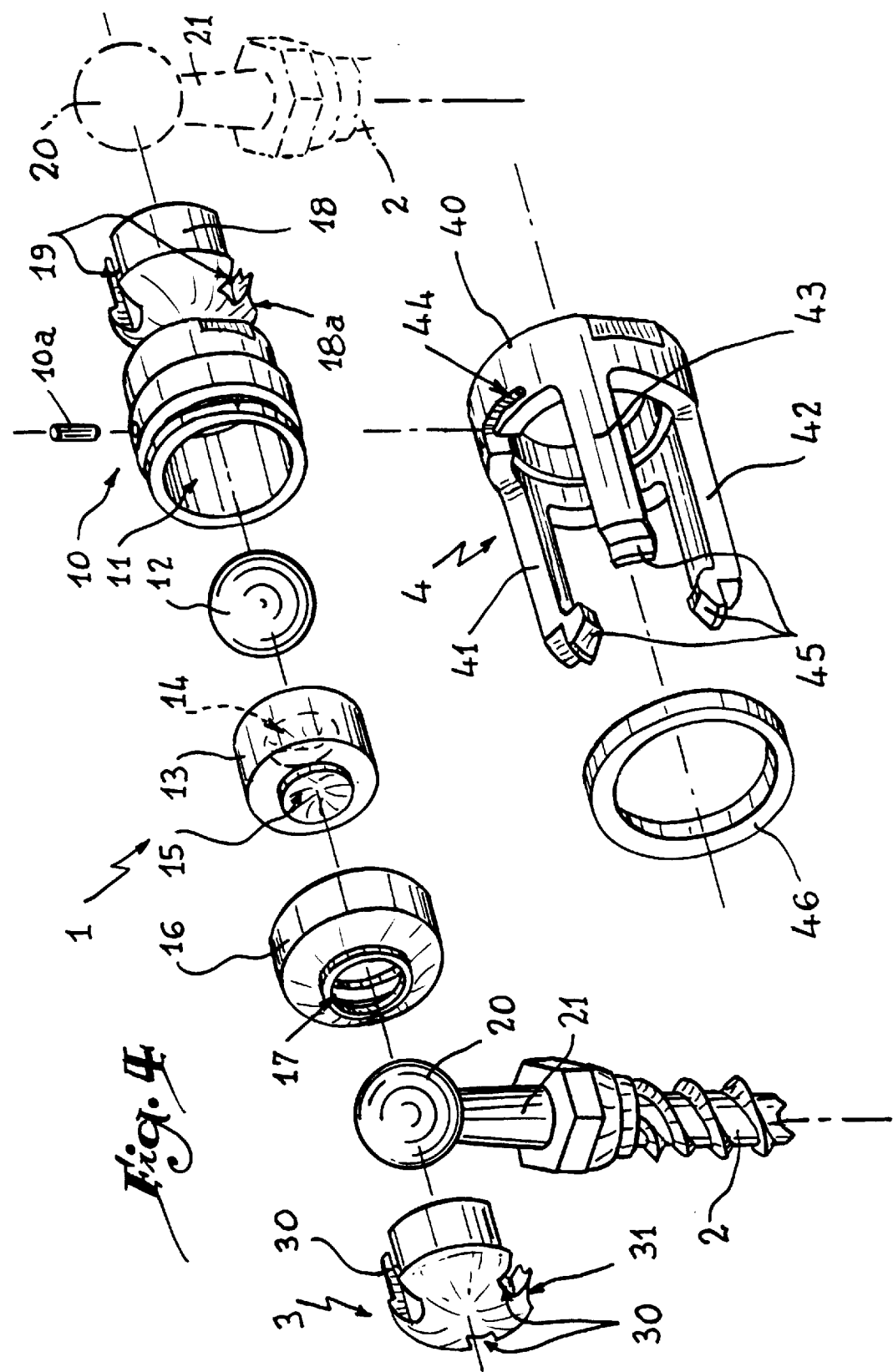
FIG. 4 is a view similar to that of FIG. 2, but showing a second variant of the securing device.

In the compression chamber 10 there slides a piston 13 having a first cavity 14, see FIG. 4, in the form of a portion of sphere whose radius is greater than that of the elastic body 12 in rest position. Opposite the cavity 14, the piston 13 comprises another cavity 15 in the form of a portion of sphere which cooperates with the ball joint 20. This screw may also constitute the end of a rigid system aiming at connecting several vertebrae together.

The sleeve 16 has an opening 17 which hermetically surrounds the cavity 15 of the piston 13 so that the latter is in direct contact with the ball joint 20.

Opposite the piston 13 there is provided a cup 3 which partially envelops the ball joint 20 of the screw 2.

It will be noted that the cap 11 extends opposite the body 12 by a cup 18 of a second securing device identical to cup 3, to cooperate with the ball joint 20 of a screw 2. The connection between two securing devices is therefore effected in one piece.

The cups 3 and 18 have an opening 31 and 18a allowing passage of the rod 21 of the screw 2 supporting the ball joint 20. The cups 3 and 18 have an inner part 32 and 18b in the form of a portion of sphere whose radius is identical to that of the ball joint 20 of each screw 2.

A connecting element 6 is provided to connect the compression chamber 10 to the cup 3.

The connecting element 6 is constituted by two elements 60 and 61 which are joined to each other via pins 7. Elements 60 and 61 comprise at each end two half-rings 62 and 63 which are joined to each other via a horizontal arm 64.

The half-rings 62 and 63 respectively comprise a curved profile 65 and 66 which comes into contact with the cup 3 or 18 and the compression chamber 10 when the two elements 60 and 61 are fixed.

It is observed that, upon assembly of the two elements 60 and 61, the half-rings 62, 63 of element 60 are in contact respectively with those 62, 63 of element 61 so that the curved profiles 65 and 66 extend over the whole periphery of the cups 3 or 18 and of the compression chamber 10. In this way, the half-ring 62 of element 60 is in contact with the half-ring 62 of element 61. The same applies for half-rings 63.

The half-rings 62 and 63 of element 60 are respectively pierced with opening holes 67 and 68, while the half-rings 62 and 63 of element 61 are respectively pierced with holes 68 and 67.

The holes 67 and 68 allow passage of the retaining pin 7 for the assembly of the elements 60 and 61 of element 6. The pins 7 comprise an elongated body 70 having a head 71 and a split point 72 allowing retention thereof in the corresponding hole 67, 68.

Figure 9:
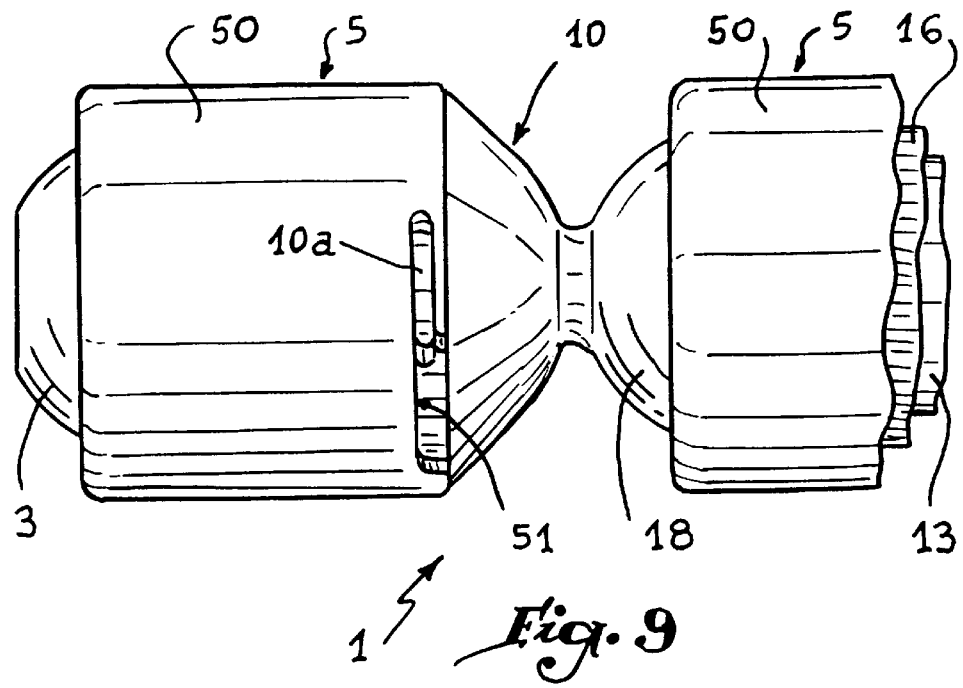

It is observed that the cup 18 extending from the compression chamber 10 cooperates, on the one hand, with the ball joint 20 of a screw 2 and, on the other hand, with a connecting element 6 of the second securing device 1, in order to constitute the device according to the invention (FIG. 9).

Figure 5:
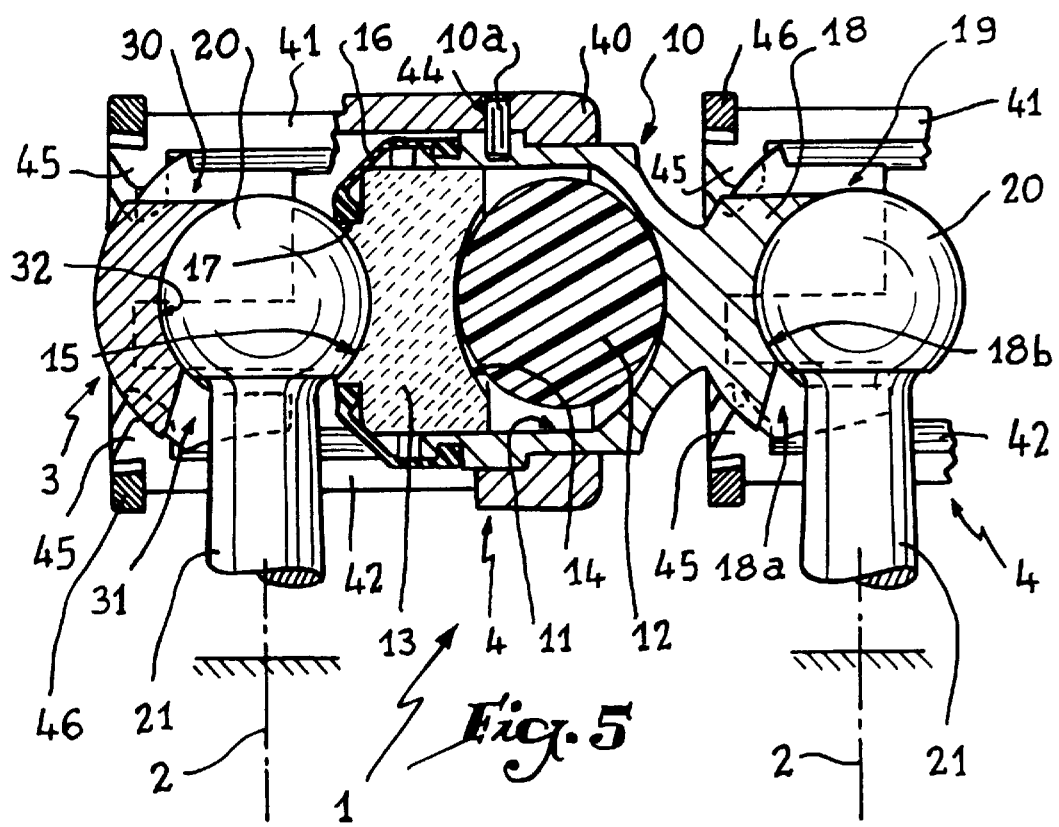
FIGS. 5 and 6 are views showing the securing device shown in FIG. 4 in assembled position.
Figure 6:
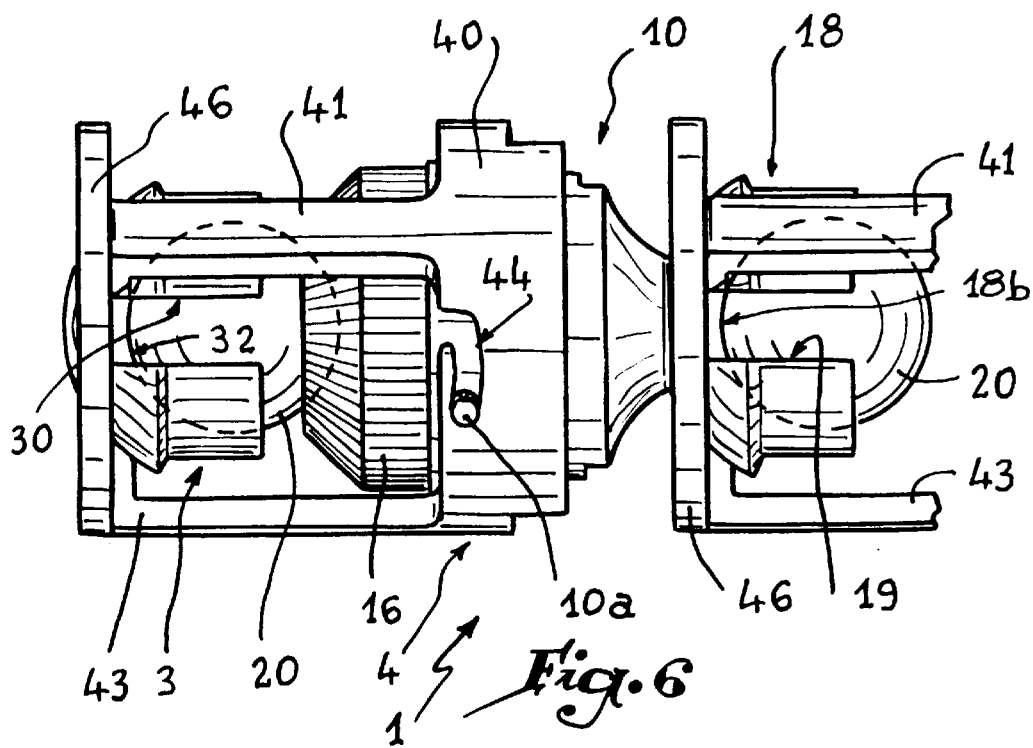

FIGS. 4 to 6 show a second variant in which each securing device 1 presents a connecting element or cage 4 of configuration different from that, 6, described previously, while all the other elements for retaining the elastic body 12 in the compression chamber 10 are identical or similar.

The cage 4 comprises a cylindrical base 40 from which three branches 41 to 43 extend longitudinally and parallel to the axis of device 1. The base 40 has a slot 44 into which penetrates at least one finger or 10a locking pin secured to the compression chamber 10 in order to constitute a bayonet-type locking device when the cage 4 is driven in rotation around said chamber.

At each free end of the branches 41 to 43 there is provided a contact or stop surface 45 which abuts against the outer face of the cup 3 via a pressure ring 46.

In fact, when the securing, device 1 is assembled, it is noted that the branches 41 to 43 cooperate, before rotation, with the grooves 30 in the cup 3 so that the stop 45 of each branch 41 to 43 comes, during rotation of the cage 4, into contact with the outer face of said cup. During this rotation, the finger 10a of the chamber 10 cooperates simultaneously with the slot 44 of the cage 4.

It will be noted that the cups 3 and 18 respectively present on their periphery grooves 30 and 19 spaced apart at regular intervals.

It will be noted that the cup 18 extending from the compression chamber 10 cooperates on the one hand, with the ball joint 20 of a screw 2 and, on the other hand, with a cage 4 of the second securing device 1 in order to constitute the device according to the invention.

It is thus observed that, between two ball joints 20 of two screws 2 previously implanted in two adjacent vertebrae, the securing devices 1 assembled with one another may pivot freely about each corresponding ball joint 20.

Figure 7:
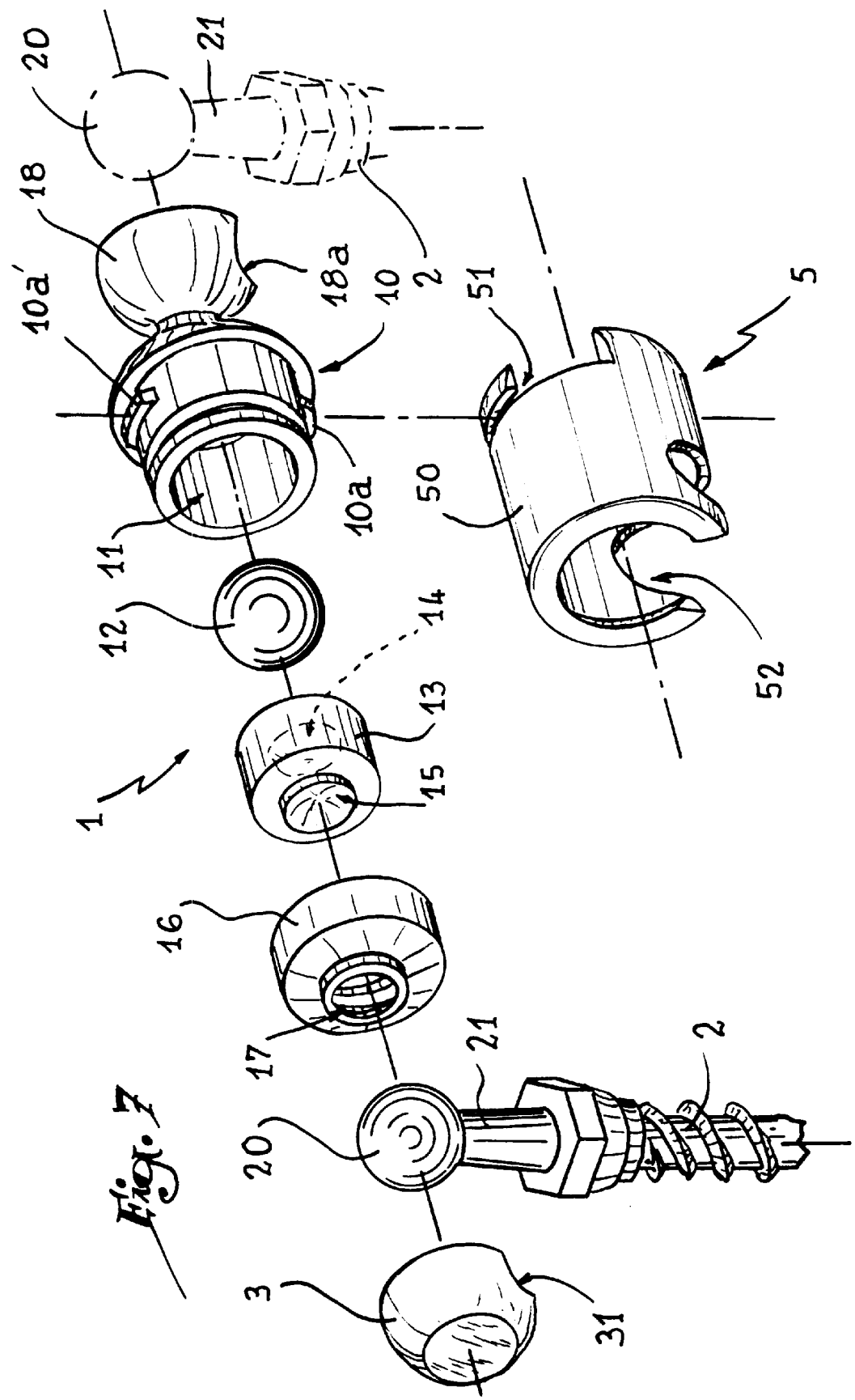
FIGS. 7 to 9 are views illustrating a third embodiment of the securing device of FIG. 1.
Figure 8:
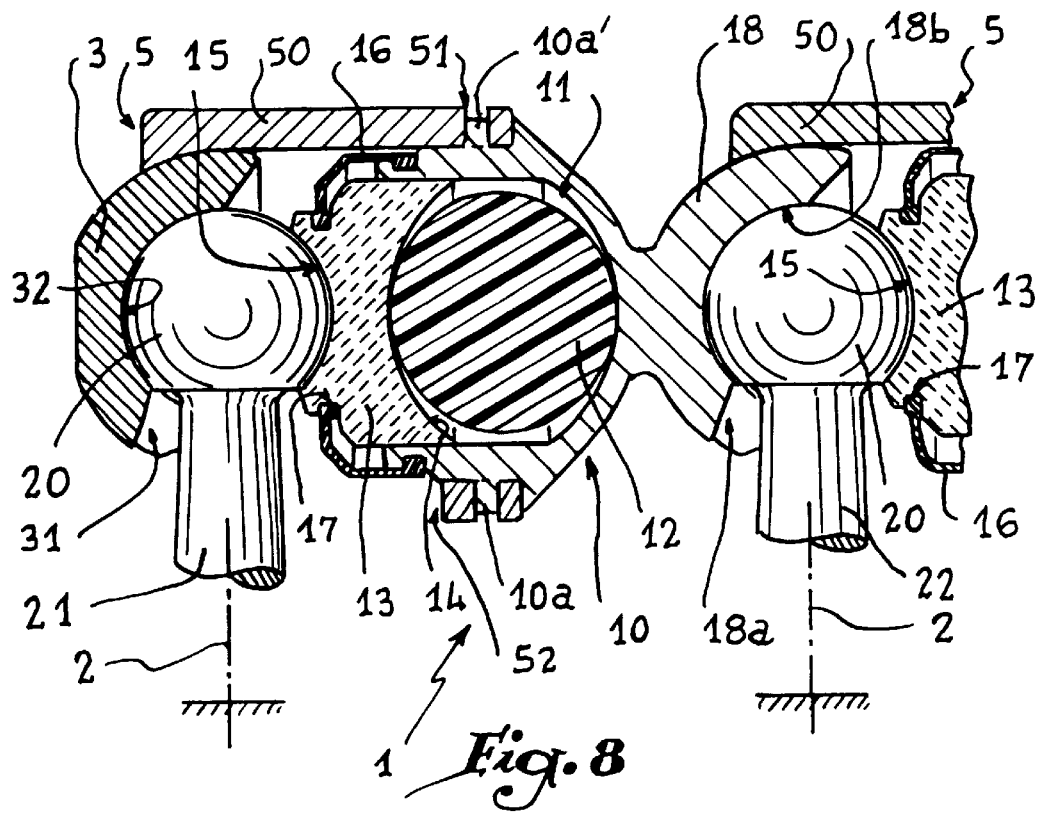

FIGS. 7 to 9 show a third variant of the device according to the invention.

Each securing device 1 has a connecting element or cage 5 whose configuration is different from that, 4, described previously, while all the other elements for positioning and retaining the elastic body 12 are identical or similar.

In fact, the elastic body 12 is maintained in the inner part 11 of the compression chamber 10 via the piston 13 and sealing sleeve 16. The ball joint 20 of the corresponding screw 2 is retained between the cavity 15 of the piston 13, and the cup 3 via the cage 5.

The cage 5 is constituted by a cylindrical muff 50 open at each of its ends. The muff 50 presents at one of its ends a slot 51, while the opposite end comprises an oblong opening 52 for the passage of the rod 21 supporting the ball joint 20 of the corresponding screw 2.

The compression chamber 10 provided with the elastic body 12, the piston 13 and the sealing sleeve 16 are thus introduced inside the cage 5 towards the opening comprising the oblong end 52 so that the cup 18 opens out outside the connector 50.

The ball joint 20 of the screw 2 and the cup 3 are placed inside the cage 5 so that said ball joint is in abutment against the cavity 15 of the piston 13. The assembly is maintained in the cage 5 by rotation thereof about its longitudinal axis to engage the finger or key 10a extending from the compression chamber 10 inside the slot 51 in order to constitute a bayonet-type locking device.

This variant of the device according to the invention constituted by at least two securing devices 1 may pivot freely about the ball joint 20 of the corresponding screw 2.

It will be noted that the cups 3 and 18 do not comprise any groove 30 and 19 as described previously in FIGS. 4 to 6, due to the configuration of the cage 5.

It is observed that the cup 18 cooperates, as already described hereinabove, on the one hand, with the ball joint 20 of a screw 2 and, on the other hand, with a cage 5 of the second securing device 1 in order to constitute the device according to the invention.

FIG. 10 shows a partial view in perspective of a securing device according to the invention during positioning. It comprises an assembly of which the ends formed by a cup 3 and a cap 11 are connected by a connecting element 6 in accordance with the one described in FIGS. 2 and 3

A ball joint 120 of the securing device 1 is provided to be screwed on a rod 121 secured to a vertebra (not shown).

This ball joint 120 and this rod 121 comprise means allowing mutual fixation by the surgeon, during the operation. To that end, the rod 121 is pierced with an axial orifice 122 extending over a part of its height.

The ball joint 120 comprises, as shown more clearly in FIG. 11, a spherical head 123 and a threaded cylindrical shank 124, likewise pierced with an axial through orifice 125 whose diameter is similar to that of the orifice 122.

The head 123 of the ball joint is provided with a cavity 126 in relation with the orifice 125, whose transverse section is polygonal, for example hexagonal.

The securing device 1 is assembled on the rod 121 previously implanted in a vertebra, in the following manner:

A guide pin 127 is firstly introduced in the orifice 122 of the rod 121. The previously assembled securing device is then descended thanks to this pin which penetrates via orifice 125 and the cavity 126 of the ball joint 120, until the free ends of the shank 124 and of the rod 121 are in contact.

A tool 128 provided with an axial through orifice 129 is descended along the guide pin 127. This tool presents a head 130 whose shape is complementary to the cavity 126. Finally, the tool 128 is rotated, which, by cooperation of the head 130 and the cavity 126, makes it possible to screw the shank of the ball joint on the rod. Such screwing induces no displacement of the securing device as a whole, since the head of the ball joint is free to rotate about the axis of its shank, with respect to the other elements of the securing device.

The tool and the guide pin are then withdrawn.

A plurality of securing devices, previously assembled together, may be mounted in similar manner, using a corresponding number of guide pins.

Assembly would be similar where the ball joint is constituted solely by its head 123, without a shank.

The man skilled in the art would then have to provide a polygonal cavity of smaller axial dimensions, so as to produce a tapping for receiving the rod, at the lower end of the head of the ball joint.

It may be provided that the compressible body 9 be replaced by an incompressible body, depending on the pathological cases.

The device for mechanically connecting and assisting vertebrae with respect to one another, constituted by at least two securing devices 1 described hereinabove, performs the role of a prosthesis for discal assistance in extradiscal position.

The device according to the invention controls the variations of relative distances in to and fro movements between two fixed points (ball joints each implanted in two close, adjacent vertebrae).

Free displacement of each securing device is understood to mean, on the one hand, a rotation about each ball joint 20, but also a rotation of each connecting element 8', 4, 5, 6 about the cups 3, 18 and, on the other hand, movements of translation along the longitudinal axis of the device which may end in transitory disconnections of the elements in the event of certain efforts.

The combination of the rotations and disconnections may end in complex movements.

What is claimed is:

1. A device for mechanically connecting and assisting vertebrae with respect to one another comprising; a least one securing device adapted to be connected to a ball joint which is adapted to extend from a vertebra, said at least one securing device including a compressible body, means for maintaining said compressible body along an axis of said at least one securing device, said means for maintaining including two end bodies adapted to house a ball joint and said compressible body therebetween, at least one of said end bodies being formed as a cup having an inner semi-spherical surface which is adapted to cover a portion of a ball joint, said end bodies being connected together by a connecting element disposed over said compressible body and over said cup, said connecting element being engaged with said two end bodies so as to maintain an axial alignment between said end bodies and being moveable over an outer surface of said cup so that said end bodies can move mutually in rotation in three spacial directions.

2. The device of claim 1 wherein only one of said end bodies is a cup, the other end body being a cap which, together with an opposing sleeve, forms a compression chamber in which said compressible body is seated.

3. The device of claim 2, including a piston disposed within said compression chamber and against said sleeve, said sleeve including an orifice through which a cavity portion of said piston extends, whereby said cavity portion of said piston is adapted to engage a ball joint.

4. The device of claim 1 wherein said connecting element includes a base from which extend three branches, said branches having free ends including a surface which engages said cup, a ring spaced from said base for connecting said branches, and said base including a slot for cooperatively receiving a locking element extending from the other of said two end bodies.

5. The device of claim 1 wherein said connecting element includes a generally cylindrical connector member having one end having a slot therein for cooperatively receiving a locking element extending from the other of said two end bodies, an opposite end of said connector member having an oblong opening therein of a size adapted to receive a ball joint therethrough.

6. The device of claim 1 wherein said connecting element includes two elements which extend toward one another from opposite sides of said two end bodies and which are connected to each other by retaining pins.

7. The device of claim 6 wherein each of said two elements includes two half rings connected to each other by an arm.

8. The device of claim 1 wherein said at least one cup includes an outer surface which is substantially semi-spherical and said connecting element including a surface for cooperatively engaging said semi-spherical outer surface of said at least one cup.

9. The device of claim 1 wherein each of said two end bodies are cups and said connecting element includes two open elastic C-shaped rings connected to each other by cross bars, each ring being disposed on an outer surface of a corresponding cup.

10. The device of claim 1, including two securing devices, and said cup of one of said two securing devices being integrally formed with the other of said two bodies of the other of said two securing devices.

11. The device of claim 1, including, in combination, a ball joint, said ball joint having an opening therethrough for receiving a guide pin for facilitating mounting of said ball joint to an anchor means having an axial orifice therethrough which anchor means is adapted to be implanted in a vertebra.

12. The device of claim 11 wherein said ball joint is provided with a cavity of polygonal cross section which is adapted to receive a tool of complementary shape to thereby secure said ball joint to said anchor means.

13. A device for mechanically connecting and assisting the vertebrae with respect to one another comprising; at least two securing devices, each securing device including a ball joint which is adapted to extend from a vertebrae, each of said securing devices including a compressible body and means for maintaining said compressible body along an axis of each securing device, each of said means for maintaining including two end bodies housing said ball joint and said compressible body of said securing device therebetween, at least one of said end bodies of each of said securing devices being formed as a cup having an inner semi-spherical surface engageable with a portion of said ball joint of said securing device and an outer surface, said end bodies of each of said securing devices being connected together by a connecting element disposed over said compressible body and over said cup of said securing device, each of said connecting elements of each of said securing device being engaged with said two end bodies of said securing means so as to maintain an axial alignment between said two end bodies thereof and being moveable over said outer surface of said cup of said securing means so that said end bodies can move mutually in rotation in three spatial directions.

14. The device of claim 3 wherein only one of said end bodies of each of said securing devices is a cup, the other end body of each of said securing devices being a cap which cooperates with an opposing sleeve to thereby form a compression chamber in which said compressible body is retained.

15. The device of claim 13, in which a piston is disposed within each of said compression chambers and against said sleeves, said sleeves including an orifice through which a cavity portion of each of said pistons extend whereby said cavity portions of said pistons engage said ball joints.

16. The device of claim 13 wherein said each of said connecting elements includes a base from which extend three branches, said branches having free ends including surfaces which engage said cups, each connecting element including a ring connecting said branches, and said base of each of said connecting elements includes a slot for cooperatively receiving a locking element extending from the other of said two end bodies of a respective securing device.

17. The device of claim 13 wherein each of said connecting elements includes a generally cylindrical connector member having one end having a slot therein for cooperatively receiving a locking element extending from the other of said two end bodies, an opposite end of said connector member having an oblong opening therein of a size to receive a ball joint therethrough.

18. The device of claim 13 wherein each of said connecting elements includes two elements which extend toward one another from opposite sides of said two end bodies of said securing device and which are connected to each other by retaining pins.

19. The device of claim 18 wherein each of said two elements includes two half rings connected to each other by an arm.

20. The device of claim 13 wherein said at least one cup of each of said securing devices includes an outer surface which is substantially semi-spherical and said connecting elements include surfaces for cooperatively engaging said semi-spherical outer surface of said at least one cup.

21. The device of claim 13 wherein each of said two end bodies of each of said securing devices are cups and said connecting elements include two open C-shaped elastic rings connected to each other by cross bars, each ring being disposed on an outer face of a corresponding cup.

22. The device of claim 13, wherein said at least one cup of one of said two securing devices are integrally formed with the other of said two bodies of the other of said two securing devices.

23. The device of claim 13, in which each of said ball joints has an opening therethrough for receiving guide pins for facilitating mounting of said ball joints to anchor means, each anchor means having an axial orifice therethrough and each anchor means being adapted to be implanted in a vertebra.

24. The device of claim 23 wherein each of said ball joints is provided with a cavity of polygonal cross section which is adapted to receive a tool of complementary shape to thereby secure said ball joints to said anchor means.

25. A method for positioning a device for mechanically connecting and assisting vertebrae with respect to one another using the device of claim 11, including the steps of:

implanting the anchor means in a vertebrae, inserting the guide pin in the axial orifice of the anchor means, placing the ball joint over the pin such that the pin extends into the opening in the ball joint, fixing the ball joint on the anchor means, and withdrawing the pin from the anchor means and the ball joint.

26. The method of claim 25 wherein the ball joint is fixed on the anchor means by screwing using a tool adapted to cover the pin, the tool having a head adapted to penetrate in a polygonal cavity of the ball joint, the tool being adapted to drive the ball joint in rotation about the pin.

* * * * *